(12) United States Patent
Tanikawa et al.

(10) Patent No.: US 7,675,675 B2
(45) Date of Patent: Mar. 9, 2010

(54) IN VIVO EXAMINATION APPARATUS

(75) Inventors: Yoshihisa Tanikawa, Tokyo (JP); Tomoaki Sato, Higashiyamato (JP); Ryoji Hyodo, Haichioji (JP)

(73) Assignee: Olympus Corporation, Tokyo (JP)

( * ) Notice: Subject to any disclaimer, the term of this patent is extended or adjusted under 35 U.S.C. 154(b) by 237 days.

(21) Appl. No.: 11/842,561

(22) Filed: Aug. 21, 2007

(65) Prior Publication Data

US 2008/0174859 A1 Jul. 24, 2008

(30) Foreign Application Priority Data

Aug. 25, 2006 (JP) ............................. 2006-229720

(51) Int. Cl.
*G02B 21/00* (2006.01)

(52) U.S. Cl. ...................... 359/368; 359/896

(58) Field of Classification Search ......... 359/368–398, 359/808–830, 896, 554–557
See application file for complete search history.

(56) References Cited

U.S. PATENT DOCUMENTS

| 5,793,524 | A | * | 8/1998 | Luloh ......................... 359/381 |
| 5,870,222 | A | * | 2/1999 | Yamamoto et al. .......... 359/368 |
| 6,392,795 | B2 | * | 5/2002 | Okada ......................... 359/368 |
| 6,437,911 | B1 | | 8/2002 | Hasegawa |
| 6,496,308 | B2 | * | 12/2002 | Yonetani et al. ............. 359/434 |
| 2004/0036962 | A1 | | 2/2004 | Brunner et al. |
| 2005/0280892 | A1 | * | 12/2005 | Nagasawa et al. ........... 359/368 |

FOREIGN PATENT DOCUMENTS

| EP | 0488023 A1 | 6/1992 |
| EP | 1186931 A2 | 3/2002 |
| JP | 2005338631 | 12/2005 |
| WO | 9741479 A1 | 11/1997 |

OTHER PUBLICATIONS

European Search Report dated Dec. 27, 2007 in corresponding EP application.
Japanese Industrial Standard, "Microscope—Screw thread for objectives," JIS B 7141 (JMMA/JSA), 2003, 12 pp.

* cited by examiner

*Primary Examiner*—Thong Nguyen
(74) *Attorney, Agent, or Firm*—Pillsbury Winthrop Shaw Pittman, LLP

(57) ABSTRACT

An in vivo examination apparatus including an objective unit capable of being readily replaced during examination is provided. The in vivo examination apparatus includes a main body, a vibration suppressor configured to suppress vibrations in an examination region of an object under examination, and an objective optical system configured to observe the examination region where the vibrations are suppressed. The objective optical system and the vibration suppressor are attached to the main body. The objective optical system is attachable to and detachable from the main body in a direction crossing an optical-axis direction of the objective optical system.

6 Claims, 9 Drawing Sheets

IN VIVO EXAMINATION APPARATUS

BACKGROUND OF THE INVENTION

1. Field of the Invention

The present invention relates to in viva examination apparatuses, and particularly to an in vivo examination apparatus including a stabilizer for allowing dynamic motion to be observed.

This application is based on Japanese Patent Application No. 2006-229720, the content of which is incorporated herein by reference.

2. Description of Related Art

Visualization of ion concentration, membrane potential, and other properties by optical microscopy using fluorescent probes has recently been employed to examine, for example, biological functions of specimens such as nerve cells and organs, particularly to observe their dynamic motion.

An example of a disclosed in vivo microscope system (in vivo examination apparatus) for observing dynamic motion has a stabilizer fitted and fixed to an outer cylindrical surface of a microscope objective unit (for example, see Japanese Unexamined Patent Application, Publication No. 2005-338631).

The above in viva microscope system, however, has the problem that the objective unit cannot be replaced during examination. Specifically, when the objective unit is replaced during examination, it alone cannot be replaced while suppressing vibrations at the examination site with the stabilizer, because the stabilizer is fixed to the cylindrical surface of the objective unit.

The above in vivo microscope system also has the problem that replacement of the objective unit is burdensome. Specifically, the objective unit must be replaced together with the stabilizer because the stabilizer is fixed to the objective unit. This replacement is burdensome because it involves additional adjustments, including focus adjustment of an alternate objective unit and the stabilizer.

BRIEF SUMMARY OF THE INVENTION

An object of the present invention, which has been created to solve the above problems, is to provide an in vivo examination apparatus including an objective unit capable of being readily replaced during examination.

To achieve the above object, the present invention provides the following solutions.

The present invention provides an in vivo examination apparatus including a main body, a vibration suppressor configured to suppress vibrations in an examination region of an object under examination, and an objective optical system configured to observe the examination region where the vibrations are suppressed. The objective optical system and the vibration suppressor are attached to the main body. The objective optical system is attachable to and detachable from the main body in a direction crossing an optical-axis direction of the objective optical system.

According to the present invention, the objective optical system can be readily replaced during examination because it can be attached to and detached from the main body in the direction crossing the optical-axis direction. The objective optical system can be attached and detached by being moved in the direction crossing the optical-axis direction while a constant distance is maintained between the main body and the object under examination. Because a constant distance is maintained between the main body and the object under examination, the vibration suppressor can continue to suppress vibrations in the examination region of the object under examination after the attachment/detachment of the objective optical system. In other words, the objective optical system can be attached to and detached from the main body during the examination while the vibration suppressor is suppressing vibrations in the examination region of the object under examination.

In the present invention, preferably, the objective optical system is attached to the main body with the vibration suppressor disposed therebetween, the objective optical system is attachable to and detachable from the main body and the vibration suppressor in the direction crossing the optical-axis direction, and the vibration suppressor is attachable to and detachable from the main body.

In this case, the vibration suppressor can continue to suppress vibrations in the examination region of the object under examination after the detachment of the objective optical system because the vibration suppressor is directly attached to the main body. The objective optical system and the vibration suppressor can be simultaneously attached to and detached from the main body by attaching and detaching the vibration suppressor to and from the main body. The relative positions of the objective optical system and the vibration suppressor can therefore be adjusted while they have been detached from the main body. The objective optical system and the vibration suppressor can then be attached to the main body with the adjusted relative positions thereof being maintained.

In the above structure, the vibration suppressor is preferably attachable to and detachable from the main body in a direction crossing the optical-axis direction.

In this case, the vibration suppressor can be readily detached from the main body without retracting the main body in the optical-axis direction.

In the present invention, the vibration suppressor preferably includes a pressing part configured to suppress the vibrations in the examination region by coming into contact therewith and a moving part configured to support the pressing part movably in the optical-axis direction.

In this case, the moving part of the vibration suppressor allows the focal point of the objective optical system to be easily adjusted to the object under examination, where vibrations are suppressed by the pressing part. The moving part also allows easy adjustment of working distance (hereinafter abbreviated as WD).

The pressing part is brought into contact with the examination region of the object under examination to suppress vibrations. The moving part allows the focal point of the objective optical system to be adjusted to the examination region, where vibrations are suppressed. In other words, the examination region, where vibrations are suppressed, is always positioned at the surface of the pressing part in contact with the object under examination. The focal point can be readily adjusted to the examination region by adjusting the relative positions of the objective optical system and the pressing part using the moving part so that the focal point lies on the contact surface.

In the present invention, preferably, the vibration suppressor includes a pressing part configured to suppress the vibrations in the examination region by coming into contact therewith and a moving part configured to support the pressing part movably in the optical-axis direction, and the pressing part is detachably attached to the moving part.

In this case, the pressing part can be readily replaced by detaching only the pressing part from the moving part.

In the present invention, preferably, the vibration suppressor includes a pressing part configured to suppress the vibrations in the examination region by coming into contact therewith and a moving part configured to support the pressing part movably in the optical-axis direction, the pressing part is detachably attached to the moving part, and the pressing part is attachable to and detachable from the moving part in a direction crossing the optical-axis direction.

In this case, the pressing part can be readily replaced because the pressing part is detachably attached to the moving part in the direction crossing the optical-axis direction. The pressing part can be readily replaced while a constant distance is maintained between the main body and the object under examination.

In the present invention, preferably, the vibration suppressor includes a pressing part configured to suppress the vibrations in the examination region by coming into contact therewith and a moving part configured to support the pressing part movably in the optical-axis direction, the in vivo examination apparatus further includes a column configured to support the main body, and the moving part is disposed between the main body and the column.

In this case, a large space can be left on the side of the main body facing away from the column. Accordingly, the examiner can operate the in vivo examination apparatus using the large space while the moving part is kept out of the way. This facilitates the examination of the object under examination.

The in vivo examination apparatus according to the present invention has the advantage that the objective optical system can be readily replaced during examination because the objective optical system and the vibration suppressor are attached to the main body and the objective optical system is attachable to and detachable from the main body in a direction crossing the optical-axis direction.

DETAILED DESCRIPTION OF THE INVENTION

First Embodiment

A first embodiment of the present invention will now be described with reference to FIGS. 1 to 5.

Figure 1:
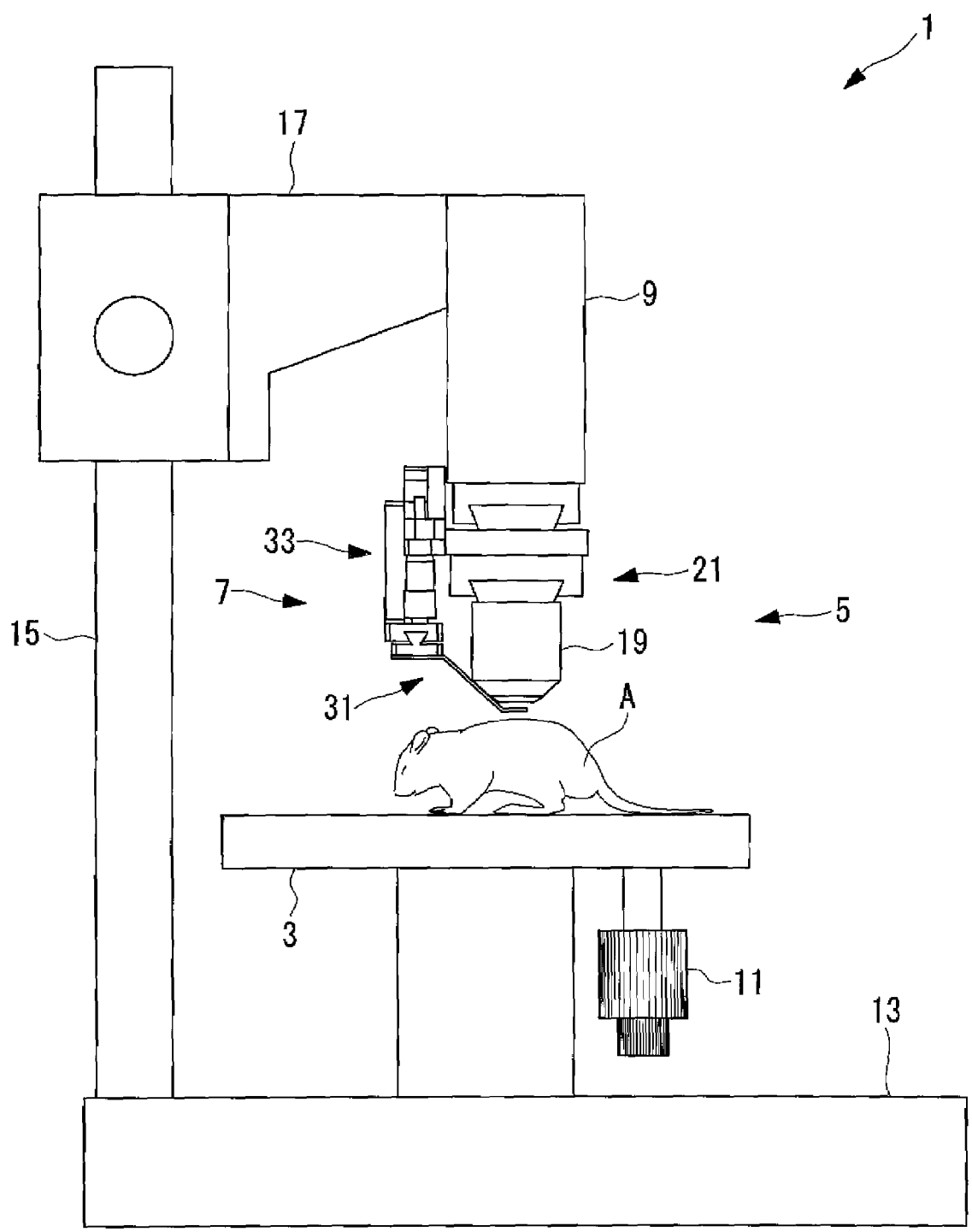
FIG. 1 is a schematic diagram of the overall structure of an in vivo microscope system according to a first embodiment of the present invention.

FIG. 1 is a schematic diagram of the overall structure of an in vivo microscope system according to this embodiment.

An in vivo microscope system (in vivo examination apparatus) 1 according to this embodiment is designed to examine a specimen (object under examination) A. Examples of the specimen A include cells, biological tissue such as muscles, and a variety of organs such as hearts and livers of mammals typified by small laboratory animals.

In FIG. 1, the in vivo microscope system 1 includes a stage 3 on which the specimen A is placed, an objective unit (objective optical system) 5 facing the specimen A on the stage 3, a stabilizer (vibration suppressor) 7 for suppressing dynamic motion of the surface of the specimen A on the stage 3, and a microscope body (main body) 9 equipped with the objective unit 5 and the stabilizer 7.

The stage 3 has an adjustment dial 11 for moving the stage 3 in two horizontal directions, for example, in the X and Y directions. The adjustment dial 11 can be operated to move the specimen A on the stage 3 in the two horizontal directions, for example, in the X and Y directions.

The microscope body 9 is attached to a column (support) 15 extending vertically from a base 13 with a raising and lowering mechanism 17 so that the microscope body 9 can be moved vertically. The objective unit 5 and the stabilizer 7 are attached to the microscope body 9.

The objective unit 5 is attached to the microscope body 9 so as to face vertically downward. The specimen A is placed on the stage 3, that is, between the objective unit 5 and the stage 3, and can be observed through the objective unit 5 positioned opposite the specimen A. The objective unit 5 includes an objective lens system 19 and an objective dovetail joint 21.

The objective lens system 19 is intended to observe the specimen A and is attached to an objective male dovetail 27 described below.

Figure 2:
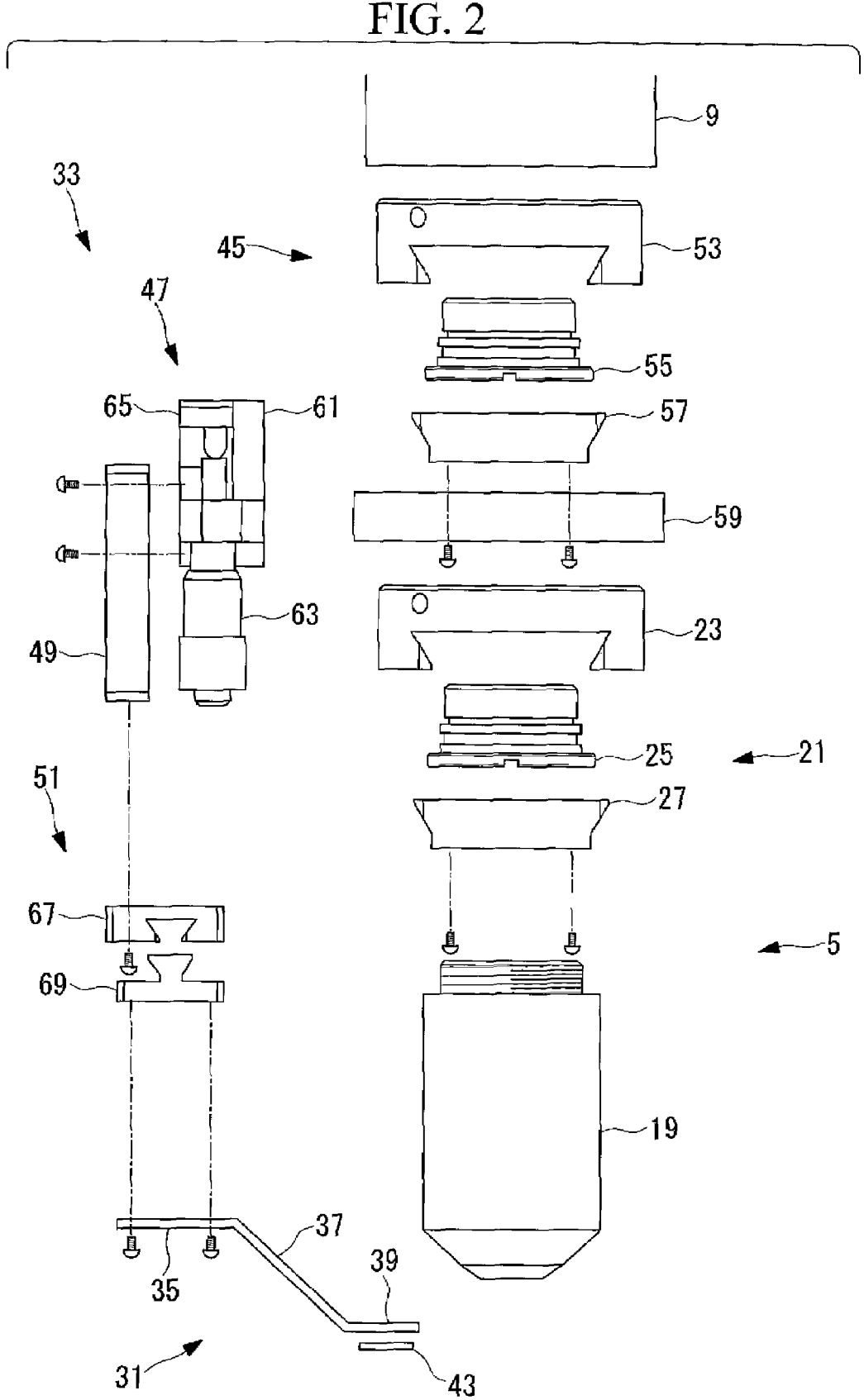
FIG. 2 is a diagram illustrating the structure of an objective unit and a stabilizer in FIG. 1.

FIG. 2 is a diagram illustrating the structure of the objective unit 5 and the stabilizer 7 in FIG. 1.

In FIG. 2, the objective dovetail joint 21 includes an objective female dovetail 23, an objective set screw 25, and the objective male dovetail 27.

The objective female dovetail 23 and the objective male dovetail 27 constitute the objective dovetail joint 21. The objective female dovetail 23 is fixed to a body plate 59 by the objective set screw 25.

The objective set screw 25 is screwed into a female screw thread formed in the body plate 59 (for example, a female screw thread according to Japanese Industrial Standards (JIS) B7141, entitled "Microscope—Screw thread for objectives"; not shown) to fix the objective female dovetail 23 to the body plate 59.

The objective male dovetail 27 and the objective female dovetail 23 constitute the objective dovetail joint 21 such that the objective male dovetail 27 can be moved in a direction crossing the optical-axis direction of the objective lens system 19, preferably, in a direction substantially perpendicular to the optical-axis direction of the objective lens system 19. The objective male dovetail 27 has a female screw thread (according to JIS B7141, entitled "Microscope—Screw thread for objectives"; not shown). The objective lens system 19 is attached to the objective male dovetail 27 by being screwed into the female screw thread.

The raising and lowering mechanism 17 can raise and lower the microscope body 9 to make the objective unit 5 and the stabilizer 7 closer to and further away from the specimen A. That is, the objective unit 5 can be moved close to and away from the specimen A for focusing.

In FIG. 2, the stabilizer 7 includes a stabilizer body 31 and a stabilizer moving mechanism (moving part) 33. The stabilizer body 31 is attached to the microscope body 9 with the stabilizer moving mechanism 33 disposed therebetween. The stabilizer body 31 includes a mounting portion 35, an arm 37, and an end portion (pressing part) 39.

The mounting portion 35 is a portion for attachment to the stabilizer moving mechanism 33. The end portion 39 is a portion for pressing the surface of the specimen A to suppress its dynamic motion. The end portion 39 extends in a direction crossing the optical-axis direction of the objective lens system 19, preferably, in a direction substantially perpendicular to the optical-axis direction of the objective lens system 19. The end portion 39 has an opening 41 (see FIG. 4) through which the surface of the specimen A is observed with its dynamic motion being suppressed. A glass cover 43 is disposed on a surface of the end portion 39 in contact with the specimen A so as to cover the opening 41. The arm 37 joins the mounting portion 35 and the end portion 39 together.

When a small-animal specimen is observed, the end portion 39 of the stabilizer 7 can be pressed against the surface of the specimen A to suppress its dynamic motion. The in vivo microscope system 1 can thus provide a blur-free observation image of the surface of the specimen A.

In FIG. 1, the stabilizer moving mechanism 33 supports the stabilizer body 31 such that it can be moved along the optical-axis direction of the objective lens system 19 relative to the objective lens system 19. The stabilizer moving mechanism 33 is disposed between the microscope body 9 and the column 15. In FIG. 2, the stabilizer moving mechanism 33 includes a body dovetail joint 45, a Z-stage 47, a moving mechanism plate 49, and a stabilizer dovetail joint 51.

The body dovetail joint 45 supports the stabilizer 7 and the objective lens system 19 so that they can be attached to and detached from the microscope body 9. The body dovetail joint 45 includes a body female dovetail 53, a body set screw 55, a body male dovetail 57, and the body plate 59.

The body female dovetail 53 and the body male dovetail 57 constitute the body dovetail joint 45. The body female dovetail 53 is fixed to the microscope body 9 by the body set screw 55.

The body set screw 55 is screwed into a female screw thread formed in the microscope body 9 (for example, a female screw thread according to JIS B7141, entitled "Microscope—Screw thread for objectives"; not shown) to fix the body female dovetail 53 to the microscope body 9.

The body female dovetail 53 and the body male dovetail 57 constitute the body dovetail joint 45 such that the body male dovetail 57 can be moved in a direction crossing the optical-axis direction of the objective lens system 19, preferably, in a direction substantially perpendicular to the optical-axis direction of the objective lens system 19. The body male dovetail 57 is fixed to the body plate 59 using screws.

The body plate 59 holds the objective female dovetail 23, the body male dovetail 57, and the Z-stage 47. The body male dovetail 57 is fixed to a surface of the body plate 59 opposite the microscope body 9, and the objective female dovetail 23 is fixed to a surface of the body plate 59 opposite the objective unit 5. The Z-stage 47 is fixed to a side surface of the body plate 59. In other words, the body male dovetail 57 is fixed to the top surface of the body plate 59 perpendicular to the optical-axis direction of the objective unit 5, and the objective female dovetail 23 is fixed to the bottom surface of the body plate 59 perpendicular to the optical-axis direction of the objective unit 5. The Z-stage 47 is fixed to the side surface, parallel to the optical-axis direction, in a direction substantially perpendicular to the optical axis.

The Z-stage 47 allows the stabilizer 7 to be moved along the optical-axis direction of the objective lens system 19 relative to the objective lens system 19. The Z-stage 47 includes a fixed plate 61, a microhead 63, and a movable plate 65.

The fixed plate 61 is fixed to the body plate 59 and is supported so that it can be moved relative to the movable plate 65. A cross roller guide (not shown) and the microhead 63 are disposed between the fixed plate 61 and the movable plate 65 so that the plates 61 and 65 can be moved relative to each other.

The movable plate 65 can be moved relative to the fixed plate 61 by rotating a knob of the microhead 63, which is fixed to the fixed plate 61.

The moving mechanism plate 49 is fixed to the movable plate 65, which supports the moving mechanism plate 49 so that it can be moved relatively to the fixed plate 61.

The moving mechanism plate 49 joins the movable plate 65 and the stabilizer dovetail joint 51 together.

The stabilizer dovetail joint 51 supports the stabilizer body 31 so that it can be attached to and detached from the stabilizer moving mechanism 33. The stabilizer dovetail joint 51 includes a stabilizer female dovetail 67 and a stabilizer male dovetail 69.

The stabilizer female dovetail 67 and the stabilizer male dovetail 69 constitute the stabilizer dovetail joint 51. The stabilizer female dovetail 67 is fixed to the moving mechanism plate 49 using screws.

The stabilizer female dovetail 67 and the stabilizer male dovetail 69 constitute the stabilizer dovetail joint 51 such that the stabilizer male dovetail 69 can be moved in a direction crossing the optical-axis direction of the objective lens system 19, preferably, in a direction substantially perpendicular to the optical-axis direction of the objective lens system 19. The stabilizer male dovetail 69 is fixed to the stabilizer body 31 using screws.

The operation of the in vivo microscope system 1 according to this embodiment will now be described.

First, the preparation procedure of the in vivo microscope system 1 according to this embodiment will be described.

First, the objective lens system 19 with a desired observation magnification is attached to the stabilizer moving mechanism 33 which is detached from the microscope body 9. Specifically, the objective male dovetail 27 fixed to the objective lens system 19 is fitted into the objective female dovetail 23 fixed to the body plate 59 of the stabilizer moving mechanism 33.

Figure 3:
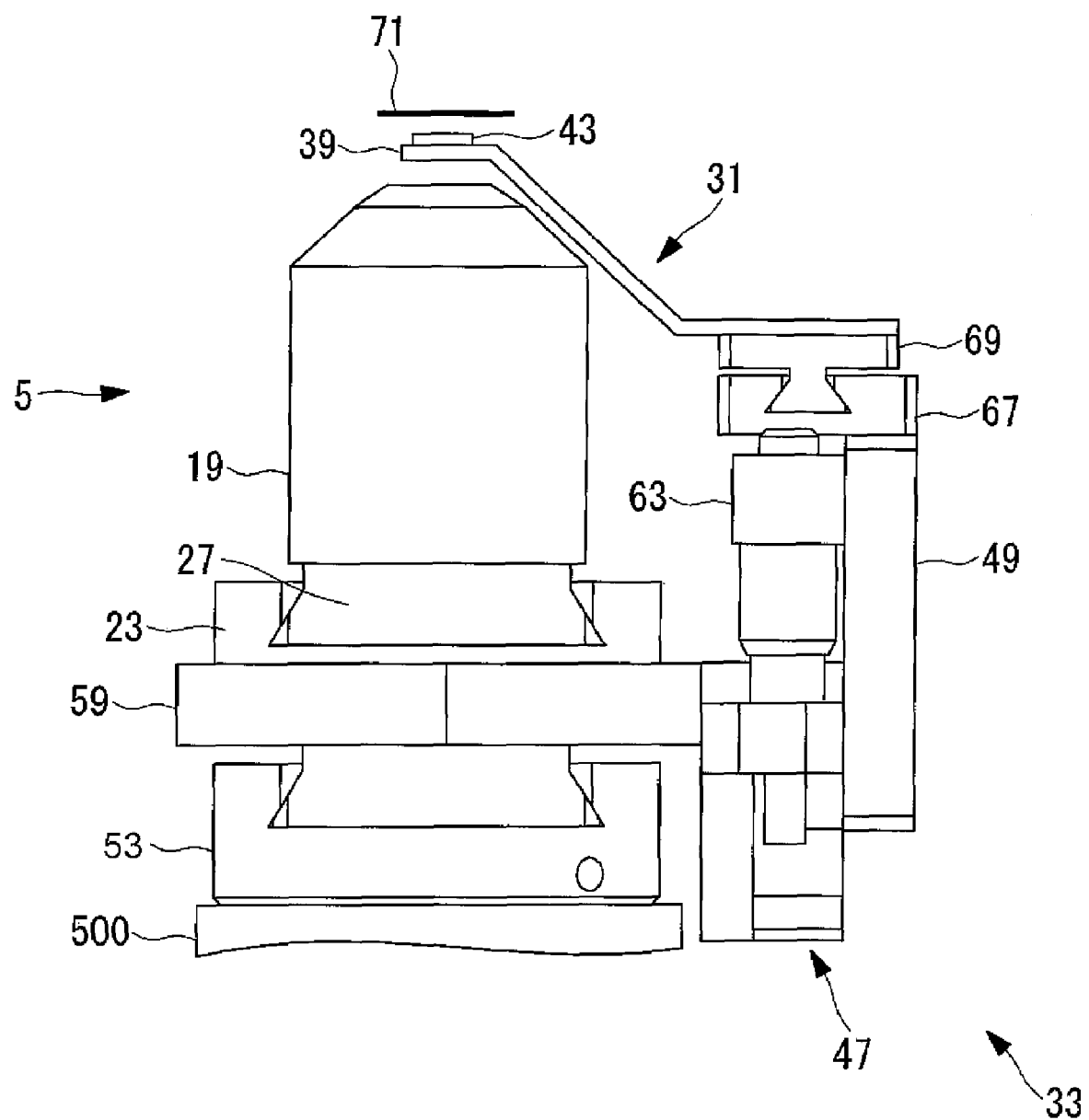
FIG. 3 is a diagram illustrating a method for focus adjustment of the objective unit and the stabilizer in FIG. 1.

FIG. 3 is a diagram illustrating a method for focus adjustment of the objective unit 5 and the stabilizer 7 in FIG. 1.

In FIG. 3, the objective unit 5 and the stabilizer moving mechanism 33 are attached to, for example, an inverted microscope 500 before the focus adjustment of the objective unit 5 and the stabilizer moving mechanism 33.

An indicator plate 71 with a cross mark, for example, is placed on top of the glass cover 43 of the end portion 39. The stabilizer body 31 is then moved along the optical-axis direction of the objective lens system 19 by rotating the knob of the microhead 63. The relative positions of the glass cover 43 on the end portion 39 and the objective lens system 19 are adjusted so that the focus (focal point) of the objective lens system 19 lies on the surface of the glass cover 43 in contact with the indicator plate 71, or the specimen A.

Figure 4:
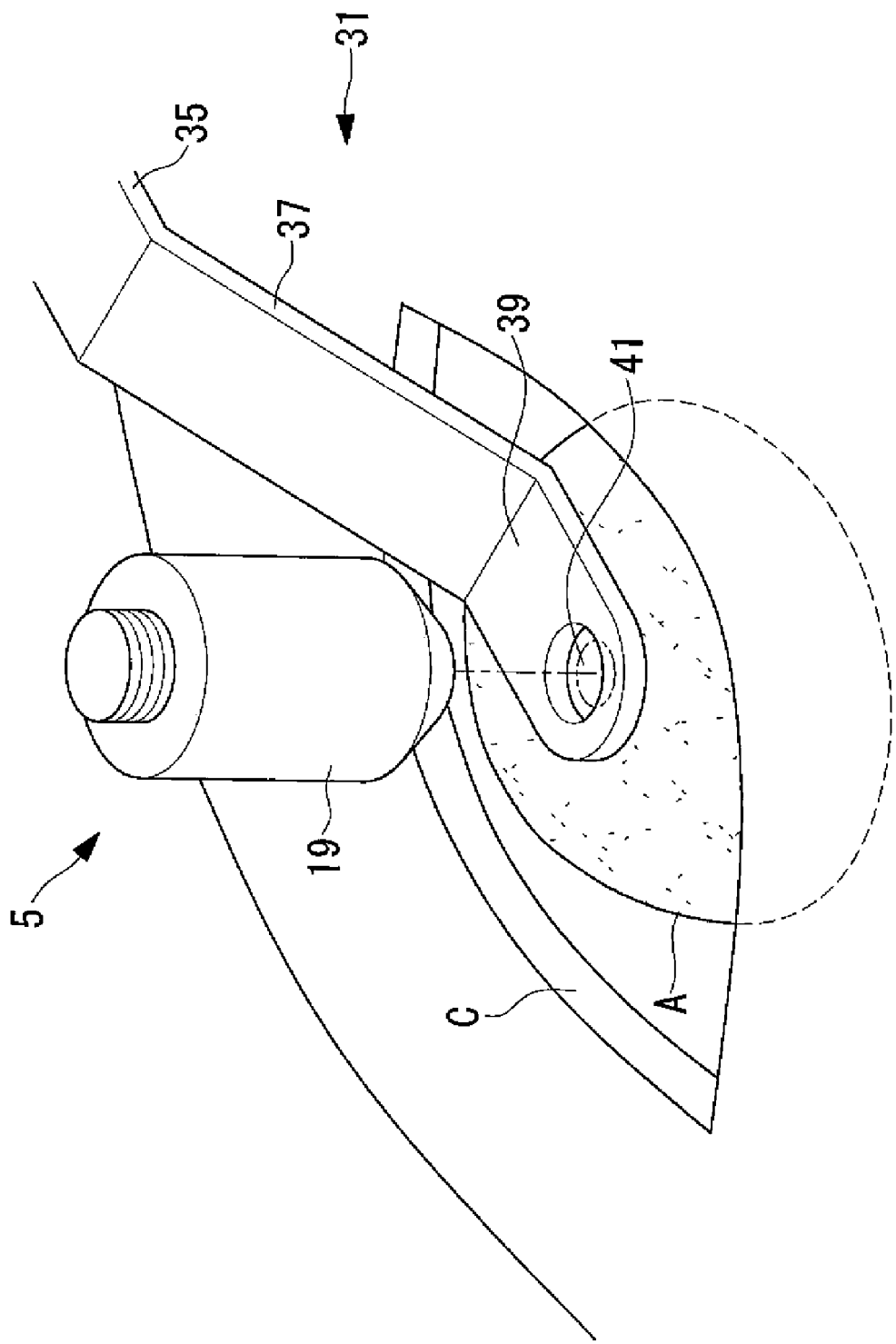
FIG. 4 is a perspective view illustrating an examination method using the in vivo microscope system in FIG. 1.

FIG. 4 is a perspective view illustrating an examination method using the in vivo microscope system 1 in FIG. 1.

Next, a small laboratory animal is placed on the stage 3. In FIG. 4, the specimen A, such as an organ, is exposed by making an incision in the skin C of the small laboratory animal. The objective unit 5 and the stabilizer moving mechanism 33 are attached to the microscope body 9 after the completion of the focus adjustment, as shown in FIG. 1. Specifically, the body male dovetail 57 fixed to the stabilizer moving mechanism 33 is fitted to the body female dovetail 53 fixed to the microscope body 9. The stabilizer moving mechanism 33 is attached to the microscope body 9 while being moved in a direction substantially perpendicular to the optical-axis direction of the microscope body 9. Accordingly, the objective unit 5 and the stabilizer moving mechanism 33 can be readily attached to the microscope body 9 with the small laboratory animal placed on the stage 3.

After the objective unit 5 is attached to the microscope body 9, the microscope body 9 is moved close to the small laboratory animal together with the stabilizer body 31 by operating the raising and lowering mechanism 17, as shown in FIG. 1. The end portion 39 of the stabilizer body 31 is moved close to the small laboratory animal and is pressed against the specimen A to suppress dynamic motion of the surface of the specimen A, as shown in FIG. 4.

The pressing of the end portion 39 against the specimen A not only suppresses the dynamic motion of the specimen A, but also provides an in-focus observation image because the focus of the objective lens system 19 has been adjusted to the surface of the glass cover 43 in contact with the specimen A in advance.

As shown in FIG. 1, the stage 3 is moved in the X and Y directions by operating the adjustment dial 11 to move the specimen A in the X and Y directions, thus bringing a target examination region into the focus of the objective lens system 19.

Although the glass cover 43 is attached to the end portion 39 as a pressing plate in the above embodiment, the structure of the end portion 39, including the presence or absence of the glass cover 43 and the shape of the end portion 39, is not limited to the above embodiment. In addition, the manner of vibration suppression is not limited to simple pressing, and various approaches can of course be employed, including vibration suppression by suction through a suction hole defined in the end portion 39 using, for example, a suction pump.

With the above structure, the objective lens system 19 can be readily replaced during examination because it can be attached to and detached from the stabilizer 7 in a direction crossing the optical-axis direction.

The objective lens system 19 can be attached to and detached from the microscope body 9 and the stabilizer 7 by being moved in the direction crossing the optical-axis direction while a constant distance is maintained between the microscope body 9 and the specimen A. Because a constant distance is maintained between the microscope body 9 and the specimen A, the stabilizer 7 can continue to suppress vibrations in the examination region of the specimen A after the attachment/detachment of the objective lens system 19. In other words, the objective lens system 19 can be attached to and detached from the microscope body 9 and the stabilizer 7 during the examination while the stabilizer 7 is suppressing vibrations in the examination region of the specimen A.

The stabilizer 7 can be readily detached from the microscope body 9 because the stabilizer 7 can be attached to and detached from the microscope body 9 in a direction crossing the optical-axis direction.

Because the stabilizer 7 can be attached to and detached from the microscope body 9 in the direction crossing the optical-axis direction, the objective unit 5 and the stabilizer body 31 can be simultaneously attached to and detached from the microscope body 9 by attaching and detaching the stabilizer body 31 to and from the microscope body 9. The relative positions of the objective lens system 19 and the end portion 39 can therefore be adjusted while they have been detached from the microscope body 9. The objective unit 5 and the stabilizer body 31 can then be attached to the microscope body 9 with the adjusted relative positions thereof being maintained.

The stabilizer moving mechanism 33 allows the focal point of the objective lens system 19 to be easily adjusted to the specimen A, where vibrations are suppressed by the end portion 39. The stabilizer moving mechanism 33 also allows easy WD adjustment.

The end portion 39 is brought into contact with the examination region of the specimen A to suppress vibrations. The stabilizer moving mechanism 33 allows the focal point of the objective lens system 19 to be adjusted to the examination region, where vibrations are suppressed. In other words, the examination region, where vibrations are suppressed, is always positioned at the surface of the end portion 39 in contact with the specimen A. The focal point can be readily adjusted to the examination region by adjusting the relative positions of the objective lens system 19 and the end portion 39 using the stabilizer moving mechanism 33 so that the focal point lies on the contact surface.

Because the stabilizer moving mechanism 33 is detachably attached to the microscope body 9 and the end portion 39 is detachably attached to the stabilizer moving mechanism 33, the stabilizer moving mechanism 33 can be readily replaced. Also, the end portion 39 can be readily replaced by detaching only the end portion 39 from the stabilizer moving mechanism 33.

The end portion 39 can be readily replaced because the end portion 39 is detachably attached to the stabilizer moving mechanism 33 in a direction crossing the optical-axis direction.

The end portion 39 can be attached to and detached from the stabilizer moving mechanism 33 by being moved in the direction crossing the optical-axis direction. Accordingly, the end portion 39 can be readily replaced while a constant distance is maintained between the microscope body 9 and the specimen A.

The specimen A can be readily examined because the stabilizer moving mechanism 33 is disposed between the microscope body 9 and the column 15.

Because the stabilizer moving mechanism 33 is disposed between the microscope body 9 and the column 15, a large space can be left on the side of the microscope body 9 facing away from the column 15. Accordingly, the examiner can operate the in vivo microscope system 1 using the large space while the stabilizer moving mechanism 33 is kept out of the way. This facilitates the examination of the specimen A.

Figure 5:
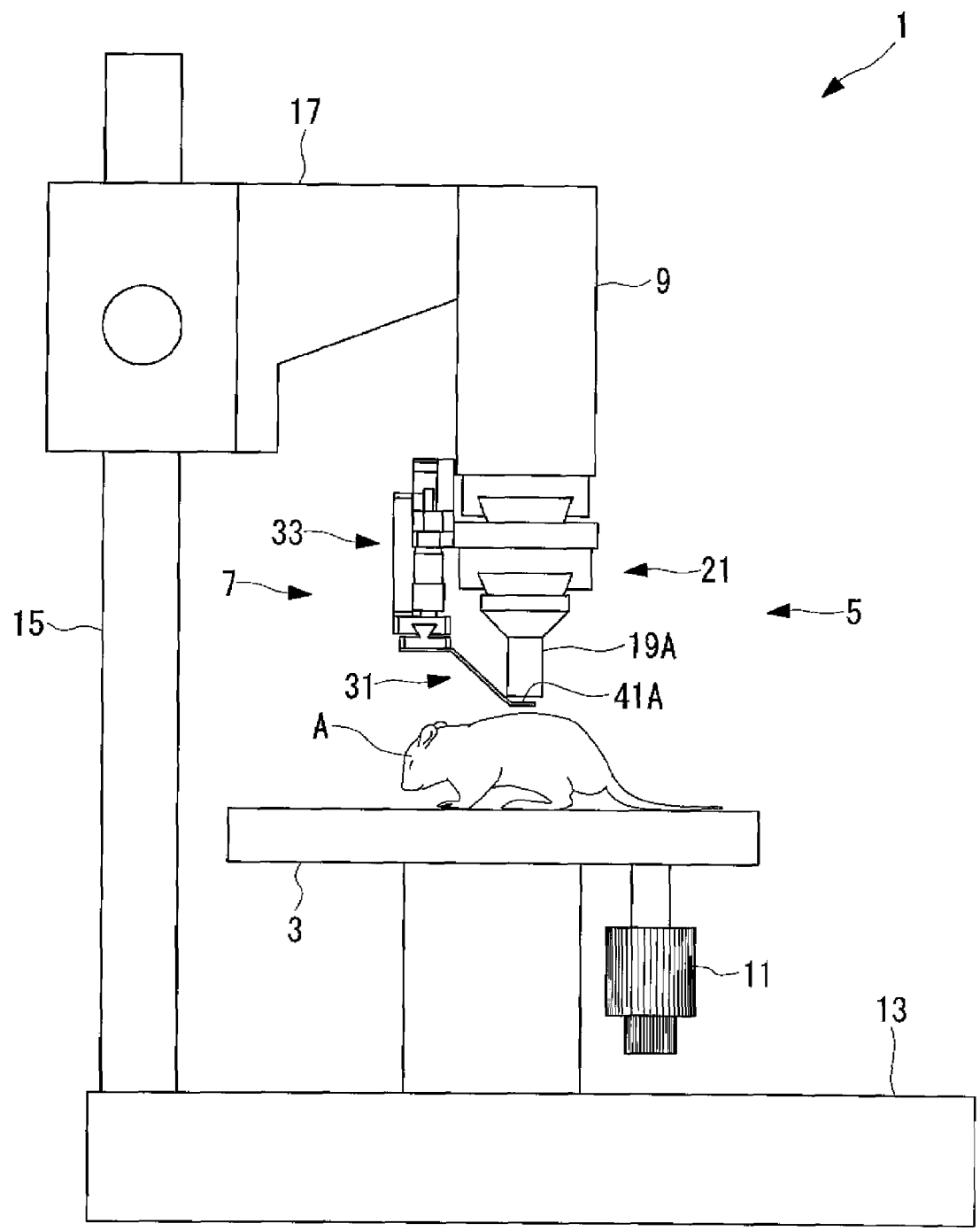
FIG. 5 is a diagram showing another example of the objective lens system used for the in vivo microscope system in FIG. 1.

FIG. 5 is a diagram showing another example of the objective lens system used for the in vivo microscope system 1 in FIG. 1.

The type of objective lens system used is not limited to any particular type; it can be the objective lens system 19 shown in FIG. 1, as in the above embodiment, or, for example, a thinner objective lens system 19A with a shorter WD (stick-shaped objective lens) shown in FIG. 5. If the objective lens system 19A is used, a notch-like opening 41A is preferably formed in the end portion 39 of the stabilizer body 31. The notch-like opening 41A allows detachment of the objective lens system 19 while preventing the front end of the objective lens system 19 from butting against the end portion 39.

The position of the stabilizer moving mechanism 33 is not limited to any particular position, and it can be disposed between the microscope body 9 and the column 15, as in the above embodiment, or at any other position.

Second Embodiment

Next, a second embodiment of the present invention will be described with reference to FIGS. 6 and 7.

An in vivo microscope system according to this embodiment has the same basic structure as that according to the first embodiment except for the structure where the stabilizer moving mechanism is fixed to the microscope body. In this embodiment, therefore, only the vicinity of the structure where the stabilizer moving mechanism is fixed to the microscope body will be described with reference to FIGS. 6 and 7, and no description will be given of the other components.

Figure 6:
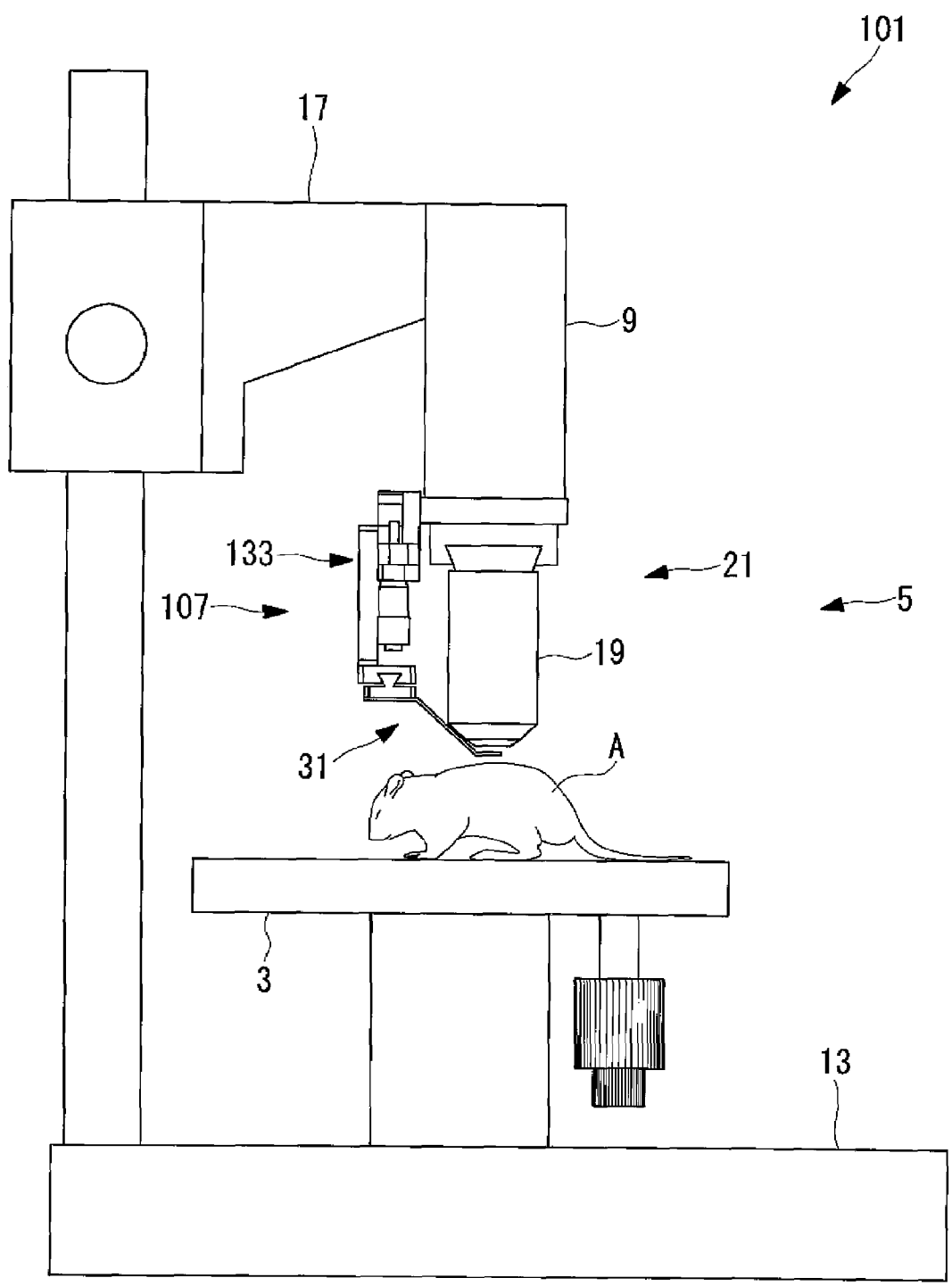
FIG. 6 is a schematic diagram of the overall structure of an in vivo microscope system according to a second embodiment of the present invention.

FIG. 6 is a schematic diagram of the overall structure of the in vivo microscope system according to this embodiment.

The same components as used in the first embodiment are indicated by the same reference numerals, and no description thereof will be given.

In FIG. 6, an in vivo microscope system (in vivo examination apparatus) 101 includes a stage 3 on which a specimen A is placed, an objective unit 5 facing the specimen A on the stage 3, a stabilizer (vibration suppressor) 107 for suppressing dynamic motion of the surface of the specimen A on the stage 3, and a microscope body 9 equipped with the objective unit 5 and the stabilizer 107.

Figure 7:
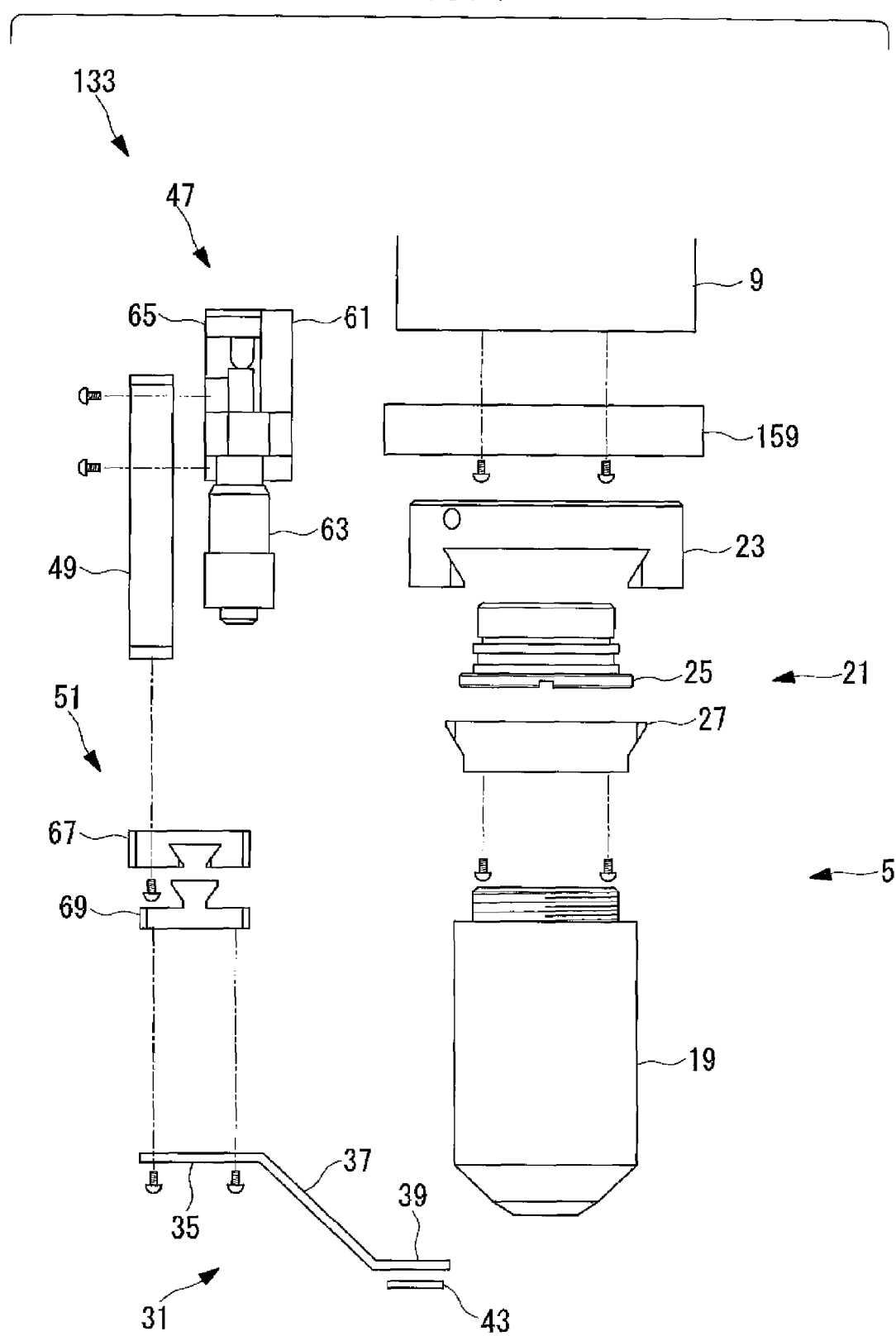
FIG. 7 is a diagram illustrating the structure of an objective unit and a stabilizer in FIG. 6.

FIG. 7 is a diagram illustrating the structure of the objective unit 5 and the stabilizer 107 in FIG. 6.

In FIG. 7, the stabilizer 107 includes a stabilizer body 31 and a stabilizer moving mechanism (moving part) 133. The stabilizer body 31 is attached to the microscope body 9 with the stabilizer moving mechanism 133 disposed therebetween. The stabilizer body 31 includes a mounting portion 35, an arm 37, and an end portion 39.

In FIG. 7, the stabilizer moving mechanism 133 supports the stabilizer body 31 such that it can be moved along the optical-axis direction of the objective lens system 19 relative to the objective lens system 19. The stabilizer moving mechanism 133 is disposed between the microscope body 9 and the column 15. In FIG. 7, the stabilizer moving mechanism 133 includes a Z-stage 47, a moving mechanism plate 49, a stabilizer dovetail joint 51, and a body plate 159.

The body plate 159 holds the objective female dovetail 23 and the Z-stage 47. The microscope body 9 is fixed to a surface of the body plate 159 opposite the microscope body 9 using screws, for example, and the objective female dovetail 23 is fixed to a surface of the body plate 159 opposite the objective unit 5 by the objective set screw 25. The Z-stage 47 is fixed to a side surface of the body plate 159. In other words, the microscope body 9 is fixed to the top surface of the body plate 159 perpendicular to the optical-axis direction of the objective unit 5, and the objective female dovetail 23 is fixed to the bottom surface of the body plate 159 perpendicular to the optical-axis direction of the objective unit 5. The Z-stage 47 is fixed to the side surface, parallel to the optical-axis direction, in a direction substantially perpendicular to the optical axis.

The operation of the in vivo microscope system 101 according to this embodiment will now be described.

In FIG. 7, first, the objective lens system 19 with a desired observation magnification is attached to the stabilizer moving mechanism 133 which is attached to the microscope body 9. Specifically, the objective male dovetail 27 fixed to the objective lens system 19 is fitted into the objective female dovetail 23 fixed to the body plate 159 of the stabilizer moving mechanism 133. Subsequently, focal adjustment of the objective unit 5 and the stabilizer moving mechanism 133 is performed as in the first embodiment.

Next, a small laboratory animal is placed on the stage 3. The specimen A, such as an organ, is exposed by making an incision in the skin C of the small laboratory animal (see FIG. 4). The microscope body 9 is then moved close to the small laboratory animal together with the stabilizer body 31 by operating the raising and lowering mechanism 17. The end portion 39 of the stabilizer body 31 is moved close to the small laboratory animal and is pressed against the specimen A (see FIG. 4) to suppress dynamic motion of the surface of the specimen A.

With the above structure, the objective unit 5 can be readily replaced during examination because it can be attached to and detached from the stabilizer 107 in a direction crossing the optical-axis direction. The objective unit 5 can be attached and detached by being moved in the direction crossing the optical-axis direction while a constant distance is maintained between the microscope body 9 and the specimen A. Because a constant distance is maintained between the microscope body 9 and the specimen A, the stabilizer 107 can continue to suppress vibrations in the examination region of the specimen A after the attachment/detachment of the objective unit 5. In other words, the objective unit 5 can be attached to and detached from the microscope body 9 and the stabilizer 107 during the examination while the stabilizer 107 is suppressing vibrations in the examination region of the specimen A.

Third Embodiment

Next, a third embodiment of the present invention will be described with reference to FIGS. 8 and 9.

An in vivo microscope system according to this embodiment has the same basic structure as that according to the first embodiment except for the structure where the stabilizer moving mechanism is fixed to the microscope body. In this embodiment, therefore, only the vicinity of the structure where the stabilizer moving mechanism is fixed to the microscope body will be described with reference to FIGS. 8 and 9, and no description will be given of the other components.

Figure 8:
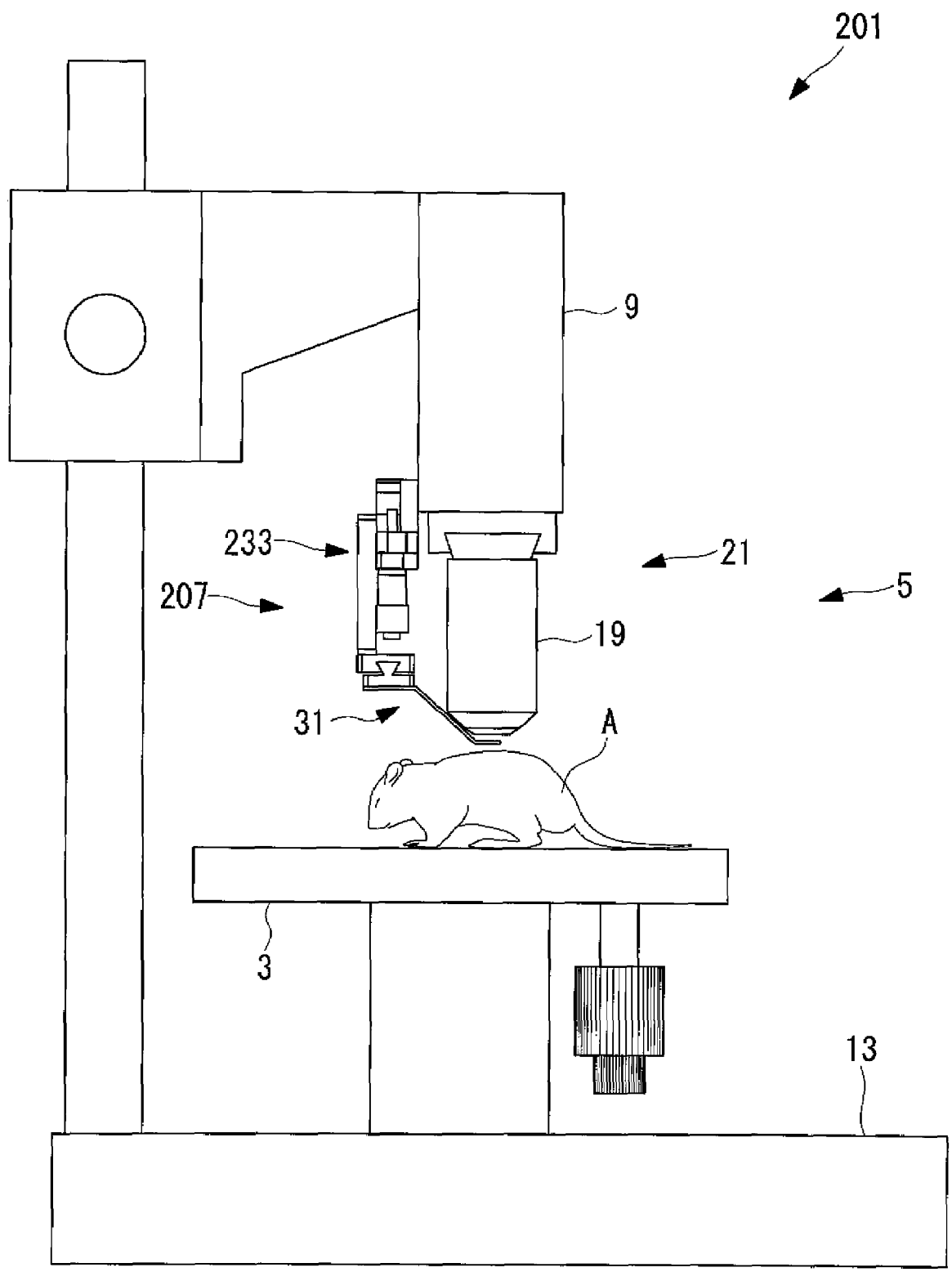
FIG. 8 is a schematic diagram of the overall structure of an in vivo microscope system according to a third embodiment of the present invention.

FIG. 8 is a schematic diagram of the overall structure of the in vivo microscope system according to this embodiment.

The same components as used in the first embodiment are indicated by the same reference numerals, and no description thereof will be given.

In FIG. 8, an in vivo microscope system (in vivo examination apparatus) 201 includes a stage 3 on which a specimen A is placed, an objective unit 5 facing the specimen A on the stage 3, a stabilizer (vibration suppressor) 207 for suppressing dynamic motion of the surface of the specimen A on the stage 3, and a microscope body 9 equipped with the objective unit 5 and the stabilizer 207.

Figure 9:
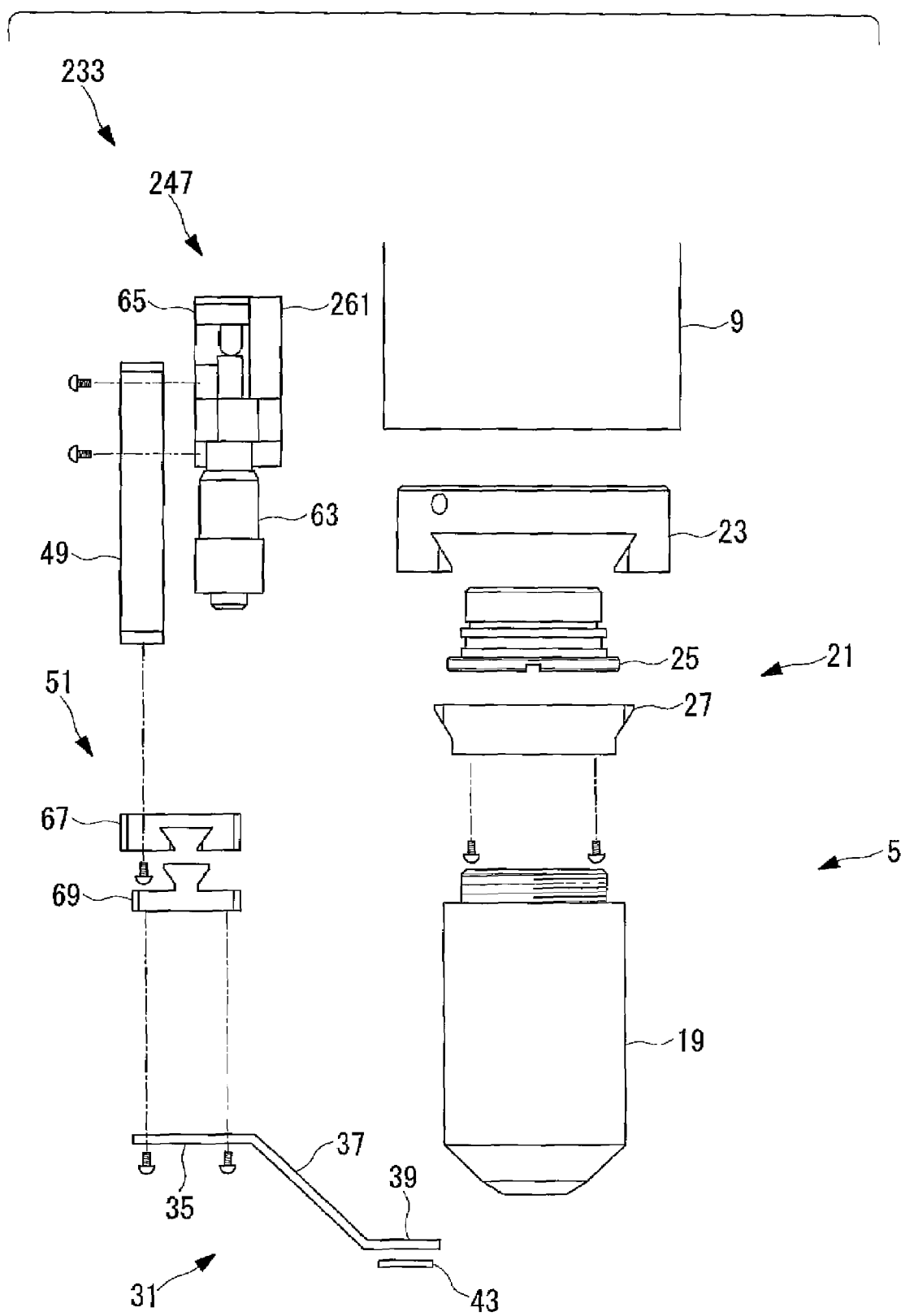
FIG. 9 is a diagram illustrating the structure of an objective unit and a stabilizer in FIG. 8.

FIG. 9 is a diagram illustrating the structure of the objective unit 5 and the stabilizer 207 in FIG. 8.

In FIG. 9, the stabilizer 207 includes a stabilizer body 31 and a stabilizer moving mechanism (moving part) 233. The stabilizer body 31 is attached to the microscope body 9 with the stabilizer moving mechanism 233 disposed therebetween. The stabilizer body 31 includes a mounting portion 35, an arm 37, and an end portion 39.

In FIG. 8, the stabilizer moving mechanism 233 supports the stabilizer body 31 such that it can be moved along the optical-axis direction of the objective lens system 19 relative to the objective lens system 19. The stabilizer moving mechanism 233 is disposed between the microscope body 9 and the column 15. In FIG. 9, the stabilizer moving mechanism 233 includes a Z-stage 247, a moving mechanism plate 49, and a stabilizer dovetail joint 51.

The Z-stage 247 allows the stabilizer 207 to be moved along the optical-axis direction of the objective lens system 19 relative to the objective lens system 19. The Z-stage 247 includes a fixed plate 261, a microhead 63, and a movable plate 65.

The fixed plate 261 is fixed to the microscope body 9 using screws, for example, and is supported so that it can be moved relative to the movable plate 65. A cross roller guide (not shown) and the microhead 63 are disposed between the fixed plate 61 and the movable plate 65 so that the plates 61 and 65 can be moved relative to each other.

No description will be given or the operation of the in vivo microscope system 201 according to this embodiment because the operation is similar to that of the in vivo microscope system 101 according to the second embodiment.

With the above structure, the objective unit 5 can be readily replaced during examination because it can be attached to and detached from the microscope body 9 in a direction crossing the optical-axis direction. The objective unit 5 can be attached and detached by being moved in the direction crossing the optical-axis direction while a constant distance is maintained between the microscope body 9 and the specimen A. Because a constant distance is maintained between the microscope body 9 and the specimen A, the stabilizer 207 can continue to suppress vibrations in the examination region of the specimen A after the attachment/detachment of the objective unit 5. In other words, the objective unit 5 can be attached to and detached from the microscope body 9 during the examination while the stabilizer 207 is suppressing vibrations in the examination region of the specimen A.

What is claimed is:

1. An in vivo examination apparatus comprising:
    a main body;
    a vibration suppressor configured to suppress vibrations in an examination region of an object under examination; and
    an objective optical system configured to observe the examination region where the vibrations are suppressed;
    wherein the objective optical system and the vibration suppressor are attached to the main body such that the objective optical system is attached to the main body with the vibration suppressor disposed therebetween;
    the objective optical system is attachable to and detachable from the main body in a direction crossing an optical-axis direction of the objective optical system; and
    the vibration suppressor comprises:
    a pressing part configured to suppress the vibrations in the examination region by coming into contact therewith; and
    a moving part configured to support the pressing part movably in the optical-axis direction.

2. The in vivo examination apparatus according to claim 1, wherein
    the objective optical system is attachable to and detachable from the main body and the vibration suppressor in the direction crossing the optical-axis direction; and
    the vibration suppressor is attachable to and detachable from the main body.

3. The in viva examination apparatus according to claim 2, wherein the vibration suppressor is attachable to and detachable from the main body in a direction crossing the optical-axis direction.

4. The in viva examination apparatus according to claim 1, wherein the pressing part is detachably attached to the moving part.

5. The in viva examination apparatus according to claim 4, wherein the pressing part is attachable to and detachable from the moving part in a direction crossing the optical-axis direction.

6. The in vivo examination apparatus according to claim 1, further comprising a column configured to support the main body, the moving part being disposed between the main body and the column.

* * * * *